US012573117B2

(12) United States Patent (10) Patent No.: US 12,573,117 B2
Jang et al. (45) Date of Patent: Mar. 10, 2026

(54) METHOD AND DEVICE FOR DEEP LEARNING-BASED PATCHWISE RECONSTRUCTION FROM CLINICAL CT SCAN DATA

(71) Applicant: Korea Advanced Institute of Science and Technology, Daejeon (KR)

(72) Inventors: In Gwun Jang, Daejeon (KR); Bong-Ju Chun, Daejeon (KR); Hyukjin Koh, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 506 days.

(21) Appl. No.: 18/101,148

(22) Filed: Jan. 25, 2023

(65) Prior Publication Data

US 2024/0119648 A1 Apr. 11, 2024

(30) Foreign Application Priority Data

Oct. 6, 2022 (KR) ........................ 10-2022-0127616

(51) Int. Cl.
*G06T 11/00* (2006.01)
*G06T 3/4046* (2024.01)
(Continued)

(52) U.S. Cl.
CPC .......... *G06T 11/008* (2013.01); *G06T 3/4046* (2013.01); *G06T 7/0012* (2013.01);
(Continued)

(58) Field of Classification Search
CPC ... G06T 11/008; G06T 3/4046; G06T 7/0012; G06T 7/11; G06T 7/136;
(Continued)

(56) References Cited

U.S. PATENT DOCUMENTS 11,315,221 B2 * 4/2022 Matsuura .............. G06F 18/214
2019/0021677 A1 * 1/2019 Grbic ........................ G06T 7/11
(Continued)

FOREIGN PATENT DOCUMENTS

JP 2007524438 A * 8/2007 .............. G06T 7/11
JP 2021-149473 A 9/2021
(Continued)

OTHER PUBLICATIONS

Thomson, et al., åNoise reduction using novel loss functions to compute tissue mineral density and trabecular bone volume fraction on low resolution QCTâ, Computerized Medical Imaging and Graphics vol. 86, Dec. 2020, 101816 (Year: 2020).*
(Continued)

*Primary Examiner* — Emily C Terrell
*Assistant Examiner* — Jordan McKenzie Elliott
(74) *Attorney, Agent, or Firm* — Christensen O'Connor Johnson Kindness PLLC

(57) ABSTRACT

Provided are a method and device for deep learning-based patch-wise three-dimensional (3D) bone microstructure reconstruction from clinical CT scan data. A computer device may be configured to segment a low-resolution skeletal image into a plurality of low-resolution image patches, to acquire a plurality of high-resolution image patches from the low-resolution image patches, respectively, using a pretrained artificial neural network, and to reconstruct a high-resolution bone microstructure by assembling and postprocessing the high-resolution image patches.

14 Claims, 9 Drawing Sheets

(51) Int. Cl.

| | |
|---|---|
| *G06T 7/00* | (2017.01) |
| *G06T 7/11* | (2017.01) |
| *G06T 7/136* | (2017.01) |
| *G16H 30/40* | (2018.01) |
| *G16H 50/20* | (2018.01) |

(52) U.S. Cl.
CPC ............... *G06T 7/11* (2017.01); *G06T 7/136* (2017.01); *G16H 30/40* (2018.01); *G16H 50/20* (2018.01); *G06T 2207/10081* (2013.01); *G06T 2207/20016* (2013.01); *G06T 2207/20021* (2013.01); *G06T 2207/20081* (2013.01); *G06T 2207/20084* (2013.01); *G06T 2207/30008* (2013.01); *G06T 2210/41* (2013.01); *G06T 2211/40* (2013.01)

(58) Field of Classification Search
CPC . G06T 2207/10081; G06T 2207/20016; G06T 2207/20021; G06T 2207/20081; G06T 2207/20084; G06T 2207/30008; G06T 2210/41; G06T 2211/40; G06T 3/4076; G06T 11/003; G16H 30/40; G16H 50/20; A61B 6/5211; A61B 6/032; A61B 6/505; G06N 3/08
See application file for complete search history.

(56) References Cited

U.S. PATENT DOCUMENTS

| | | | |
|---|---|---|---|
| 2023/0033442 A1* | 2/2023 | Xiang ..................... | G06N 3/088 |
| 2024/0104796 A1* | 3/2024 | Holbrook .................. | G06T 7/11 |

FOREIGN PATENT DOCUMENTS

| | | |
|---|---|---|
| KR | 10-2017-0003476 A | 1/2017 |
| KR | 1017852150000 B1 | 10/2017 |
| KR | 10-2019-0040586 A | 4/2019 |
| KR | 10-2084138 B1 | 3/2020 |

OTHER PUBLICATIONS

Indranil Guha, Syed Ahmed Nadeem, Chenyu You, Xiaoliu Zhang, Steven M. Levy, Ge Wang, James C. Torner, Punam K. Saha, "Deep learning based high-resolution reconstruction of trabecular bone microstructures from low-resolution CT scans using GAN-CIRCLE," (Year: 2020).*

Shorten, C., Khoshgoftaar, T.M. A survey on Image Data Augmentation for Deep Learning. J Big Data 6, 60 (2019). https://doi.org/10.1186/s40537-019-0197-0 (Year: 2019).*

Thomson, et al., Noise reduction using novel loss functions to compute tissue mineral density and trabecular bone volume fraction on low resolution QCT, Computerized Medical Imaging and Graphics vol. 86, Dec. 2020, 101816 (Year: 2020).*

Hambli, R., Katerchi, H. & Benhamou, CL. Multiscale methodology for bone remodelling simulation using coupled finite element and neural network computation. Biomech Model Mechanobiol 10, 133â145 (2011) (Year: 2011).*

Extended European Search Report mailed Sep. 18, 2023, issued in corresponding Application No. EP 23152812.6, filed Jan. 23, 2023, 9 pages.

International Search Report mailed Jun. 28, 2023, issued in corresponding International Application No. PCT/KR2022/020533, filed Dec. 16, 2022, 6 pages.

Lai, C., et al., "Image super-resolution based on segmentation and classification with sparsity", 2016 2nd IEEE International Conference on Computer and Communications, Oct. 14, 2016, pp. 563-567.

Steybe, D., et al., "Automated segmentation of head CT scans for computer-assisted craniomaxillofacial surgery applying a hierarchical patch-based stack of convolutional neural networks," International Journal of Computer Assisted Radiology and Surgery (2022) 17(11): 2093-2101.

Yunpeng, L., et al., "Automatic Segmentation of Shoulder Joint in MRI Using Patch-Based and Fully Convolutional Networks," 2018 25th IEEE International Conference on Image Processing (ICIP), Oct. 7, 2018, pp. 3508-3512.

Bjornsson, P.A., et al., "Automated femur segmentation from computed tomography images using a deep neural network," arxiv.org, Cornell University Library, Ithaca, NY 14853, Jan. 28, 2021.

Hambli, R., et al., "Multiscale methodology for bone remodelling simulation using coupled finite element and neural network computation," Biomech Model Mechanobiol (2011) 10:133-145.

* cited by examiner

FIG. 2

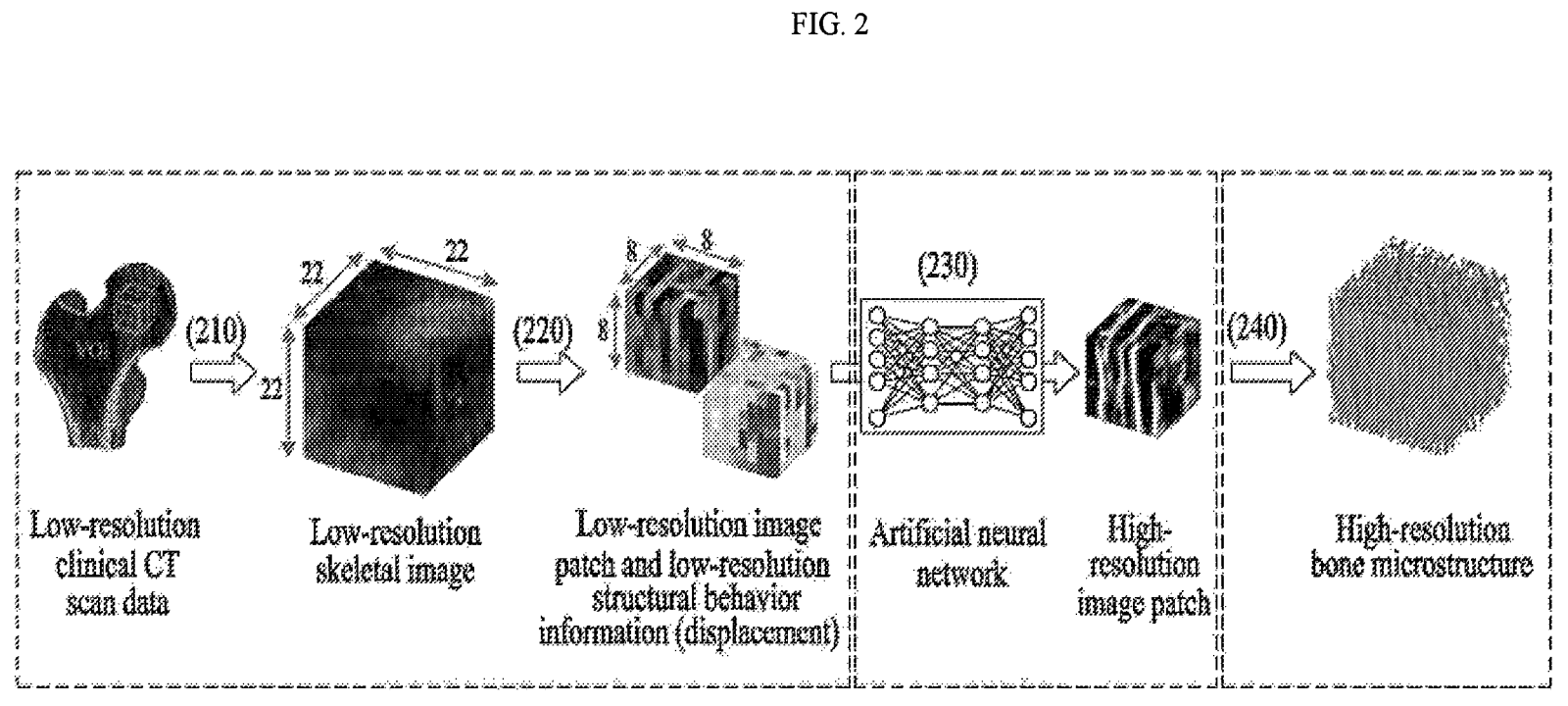

Low-resolution clinical CT scan data (210)

Low-resolution skeletal image (220)

Low-resolution image patch and low-resolution structural behavior information (displacement)

(230)

Artificial neural network

High-resolution image patch (240)

High-resolution bone microstructure

Adaptive thresholding

Computation of threshold value $$s.t \ \ \rho_{LR} = \frac{\Sigma \rho_{fit}}{N_{HR}}$$

$\rho_{fit}$ $\rho_{LR}$

Assembled image

Low-resolution skeletal image

METHOD AND DEVICE FOR DEEP LEARNING-BASED PATCHWISE RECONSTRUCTION FROM CLINICAL CT SCAN DATA

CROSS-REFERENCE TO RELATED APPLICATION

This application claims the priority benefit of Korean Patent Application No. 10-2022-0127616, filed on Oct. 6, 2022, in the Korean Intellectual Property Office, the disclosure of which is incorporated herein by reference in its entirety.

BACKGROUND

1. Field of the Invention

The following description of various example embodiments relates to a method and device for deep learning-based patch-wise three-dimensional (3D) reconstruction from clinical CT scan data.

2. Description of the Related Art

Osteoporosis is a representative degenerative disease and has no specific subjective symptoms. Although the prevalence of osteoporosis is increasing due to the aging society, only a small number of patients are aware of osteoporosis. In general, osteoporosis is recognized only after occurrence of a fracture, which makes a timely and effective medical response difficult. Also, an osteoporotic fracture may cause a serious disability and reduce the quality of individual life. After the osteoporotic fracture, many patients lose their ability to function. In addition, some patients may die when a hip fracture occurs. In Korea, the number of osteoporosis patients has been steadily increasing and it is highly likely that osteoporosis will emerge as a major social problem. According to studies to date, bone strength damaged by osteoporosis cannot be restored to its original level. This is the result of being unable to restore the connectivity of lost bone microstructure that is an irreversible characteristic of a bone remodeling process. That is, it is very important to prevent loss of bone microstructure caused by osteoporosis and, based thereon, early diagnosis of osteoporosis is clinically important.

Osteoporosis is defined as a condition in which bone strength is reduced due to a decrease in a bone mass and a qualitive degradation in a bone microstructure and bone strength represents a force that resists against fracture of bone. Since the bone strength is determined by "bone mass" that is a total amount of bone and "bone quality" such as a bone microstructure, the above two items of information need to be acquired for accurate diagnosis of osteoporosis. Currently, diagnosis of osteoporosis is performed by measuring bone mineral density (BMD) using various radiographic imaging devices and a representative imaging device includes dual energy X-ray absorptiometry (DXA), quantitative computed tomography (QCT), and the like. Such imaging devices may measure bone mass information by an X-ray attenuation rate, but may not acquire bone quality information, such as a bone microstructure, due to a low resolution of 600 μm. In this bone mass-based diagnosis of osteoporosis, two patients with different bone quality are diagnosed with the same level of osteoporosis if the bone mass is the same. There is a probability of misdiagnosis or overdiagnosis in a diagnosis method in which information of bone quality lacks. This issue has been steadily reported in clinical practice. Therefore, there is a need for development of a novel osteoporosis diagnostic method based on quantitative bone strength evaluation that includes bone quality information.

When evaluating the bone strength, a bone microstructure is a factor that has a great influence. The bone strength may be evaluated with higher accuracy when a 3D bone microstructure is considered together rather than when BMD information alone is considered. Also, clinical study has been published that more accurate diagnosis of osteoporosis may be performed when BMD measurement and bone microstructure analysis are performed together. That is, although bone microstructure information is required for reliable diagnosis of osteoporosis, it is currently impossible to acquire a high-resolution skeletal image capable of expressing the bone microstructure due to a high radiation exposure, a low signal-to-noise (SNR) ratio, a long imaging time, and limitation of an imaging area.

As securing of an image resolution through hardware improvement has reached its limits, technology for improving a resolution through postprocessing of an image acquired through an imaging device is being actively researched. Corresponding technology for high-resolution of an image is largely classified into deep learning-based technology and topology optimization-based technology.

Deep learning-based image reconstruction technology actively applies to images of various soft tissues, such as the brain and the like. Here, in the case of a high-resolution of a skeletal image that is a hard tissue, it is very difficult to successfully train an artificial neural network due to a bone microstructure in a complex shape and a high-resolution magnification is currently limited to a maximum of four times. In addition, due to a difficulty in acquiring a high-resolution skeletal image, it is difficult to build a training dataset. Also, no cases of successfully applying deep learning-based technology to a skeletal image have been reported yet.

Topology optimization-based image reconstruction technology reconstructs a bone microstructure with maximum stiffness through redistribution of BMD under given bone mass constraints based on Wolff's law that bone remodeling is a process of changing the bone microstructure to make it possible to withstand external load with minimum mass. The topology optimization-based technology shows a high-resolution magnification (around 10 times) and an accurate bone strength evaluation accuracy, but has limitations in clinical application since an excessive computation time is used due to a repetitive finite element analysis.

SUMMARY

Various example embodiments provide deep learning-based bone microstructure reconstruction technology for quick and accurate diagnosis of diseases related to a skeletal system in clinical practice.

Various example embodiments provide a method and device for deep learning-based patch-wise three-dimensional (3D) bone microstructure reconstruction from clinical CT scan data.

According to various example embodiments, a method of a computer device may include segmenting a low-resolution skeletal image into a plurality of low-resolution image patches; acquiring a plurality of high-resolution image patches from the low-resolution image patches, respectively, using a pretrained artificial neural network; and reconstructing a high-resolution bone microstructure by assembling and postprocessing the high-resolution image patches.

According to various example embodiments, a computer device may include a memory; and a processor configured to connect to the memory and to execute at least one instruction stored in the memory. The processor may be configured to segment a low-resolution skeletal image into a plurality of low-resolution image patches, to acquire a plurality of high-resolution image patches from the low-resolution image patches, respectively, using a pretrained artificial neural network, and to reconstruct a high-resolution bone microstructure by assembling and postprocessing the high-resolution image patches.

According to various example embodiments, in a non-transitory computer-readable recording medium storing instructions that, when executed by a processor, cause the processor to perform a method of acquiring a high-resolution bone microstructure, the method may include segmenting a low-resolution skeletal image into a plurality of low-resolution image patches; acquiring a plurality of high-resolution image patches from the low-resolution image patches, respectively, using a pretrained artificial neural network; and reconstructing a high-resolution bone microstructure by assembling and postprocessing the high-resolution image patches.

According to various example embodiments, it is possible to quickly and accurately reconstruct a 3D high-resolution bone microstructure from low-resolution clinical CT scan data using an artificial neural network. Here, since it is possible to minimize occurrence of a discontinuous structure by assembling and postprocessing high-resolution image patches acquired through the artificial neural network, and to apply an individual characteristic of a patient, patient-specific bone strength evaluation may be performed with higher accuracy than before.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

These and/or other aspects, features, and advantages of the invention will become apparent and more readily appreciated from the following description of embodiments, taken in conjunction with the accompanying drawings of which:

FIG. 2 illustrates an example of an operational characteristic of a computer device of FIG. 1;

FIG. 7 illustrates an example of an operation of reconstructing a 3D bone microstructure by assembling and postprocessing high-resolution image patches of FIG. 6;

FIG. 9 illustrates an example of adaptive thresholding of FIG. 7.

DETAILED DESCRIPTION

Hereinafter, example embodiments will be described with reference to the accompanying drawings.

Figure 1:
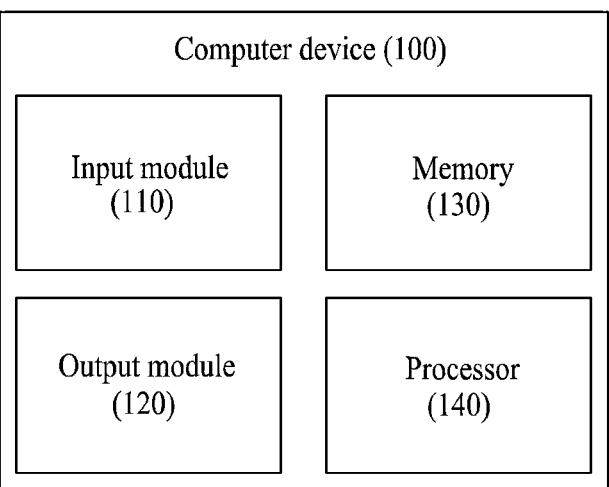
FIG. 1 is a diagram illustrating a computer device for patch-wise three-dimensional (3D) bone microstructure reconstruction according to various example embodiments.

FIG. 1 is a diagram illustrating a computer device 100 for patch-wise three-dimensional (3D) bone microstructure reconstruction according to various example embodiments. FIG. 2 illustrates an example of an operational characteristic of the computer device 100 of FIG. 1.

Referring to FIG. 1, the computer device 100 may include at least one of an input module 110, an output module 120, a memory 130, and a processor 140. In some example embodiments, at least one of components of the computer device 100 may be omitted and at least one another component may be added. In some example embodiments, at least two of the components of the computer device 100 may be implemented as a single integrated circuitry.

The input module 110 may receive a signal to be used for at least one component of the computer device 100. The input module 110 may include at least one of an input device configured for a user to directly input a signal to the computer device 100, a sensor device configured to sense an ambient change and to generate a signal, and a reception device configured to receive a signal from an external device. For example, the input device may include at least one of a microphone, a mouse, and a keyboard. In some example embodiments, the input device may include at least one of a touch circuitry set to sense a touch and a sensor circuitry set to measure strength of a force generated by the touch.

The output module 120 may output information to an outside of the computer device 100. The output module 120 may include at least one of a display device configured to visually output information, an audio output device configured to output the information as an audio signal, and a transmission device configured to wirelessly transmit the information. For example, the display device may include at least one of a display, a hologram device, and a projector. For example, the display device may be implemented as a touchscreen by being assembled to at least one of the touch circuitry and the sensor circuitry of the input module 110. For example, the audio output device may include at least one of a speaker and a receiver.

According to an example embodiment, the reception device and the transmission device may be implemented as a communication module. The communication module may communicate with an external device in the computer device 100. The communication module may establish a communication channel between the computer device 100 and the external device and may communicate with the external device through the communication channel. Here, the external device may include at least one of a vehicle, a satellite, a base station, a server, and another computer system. The communication module may include at least one of a wired communication module and a wireless communication module. The wired communication module may communicate with the external device in a wired manner through connection to the external device in a wired manner. The wireless communication module may include at least one of a near-field communication module and a far-field communication module. The near-field communication module may communicate with the external device using a near-field communication method. For example, the near-field communication method may include at least one of Bluetooth, wireless-fidelity (WiFi) direct, and infrared data association (IrDA). The far-field communication module may communicate with the external device using a far-field communication method. Here, the far-field communication module may communicate with the external device through a network. For example, the network may include at least one of a cellular network, the Internet, and a computer network such as a local area network (LAN) and a wide area network (WAN).

The memory 130 may store a variety of data used by at least one component of the computer device 100. For example, the memory 130 may include at least one of a volatile memory and a non-volatile memory. The data may include at least one program and input data or output data related thereto. The program may be stored in the memory 130 as software that includes at least one command and may include at least one of an operating system, middleware, and an application.

The processor 140 may control at least one component of the computer device 100 by executing the program of the memory 130. Through this, the processor 140 may perform data processing or operations. Here, the processor 140 may execute the instruction stored in the memory 130.

According to various example embodiments, referring to FIG. 2, the computer device 100 may reconstruct a 3D high-resolution bone microstructure from a low-resolution skeletal image. In detail, in operation 210, the processor 140 may acquire a low-resolution skeletal image corresponding to a volume of interest (VOI) from low-resolution clinical CT scan data. In operation 220, the processor 140 may acquire low-resolution image patches by sampling the low-resolution skeletal image. Here, the processor 140 may acquire low-resolution structural behavior information (e.g., displacement) on each of the low-resolution image patches. Here, the structural behavior information may represent a displacement of a finite model node of VOI when an external load is applied. In operation 230, the processor 140 may acquire a plurality of high-resolution image patches from the low-resolution image patches, respectively, using a pretrained artificial neural network. Here, the artificial neural network may be pretrained based on a learning dataset that is generated from high-resolution skeletal images reconstructed through topology optimization-based skeletal image reconstruction technology. In operation 240, the processor 140 may reconstruct a high-resolution bone microstructure by assembling and postprocessing the high-resolution image patches. Here, the processor 140 may perform postprocessing of repeatedly applying density filtering and adaptive thresholding to an assembled image to clearly express a connectivity between the high-resolution image patches and to remove a discontinuity between the high-resolution image patches.

Figure 3:
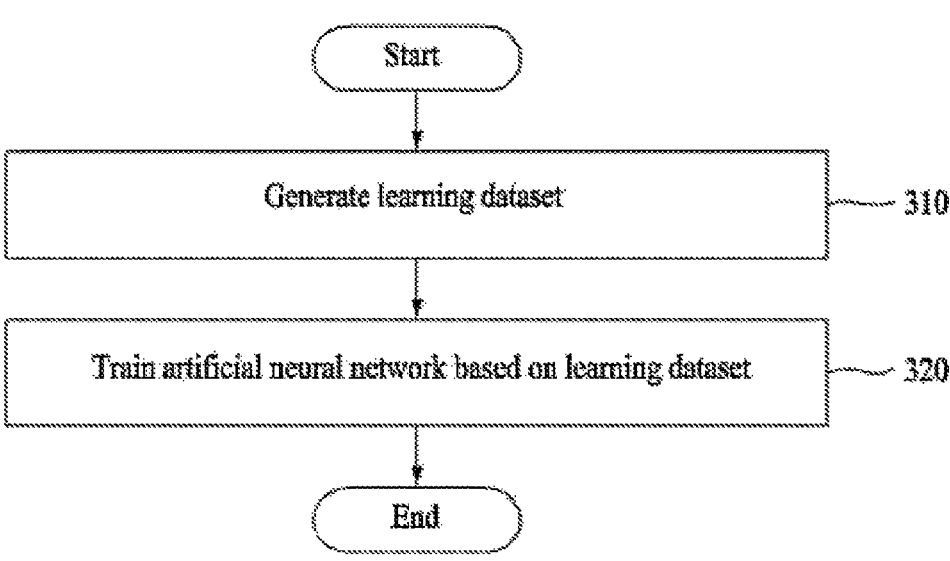
FIG. 3 is a flowchart illustrating a method of training an artificial neural network of a computer device according to various example embodiments.
Figure 4:
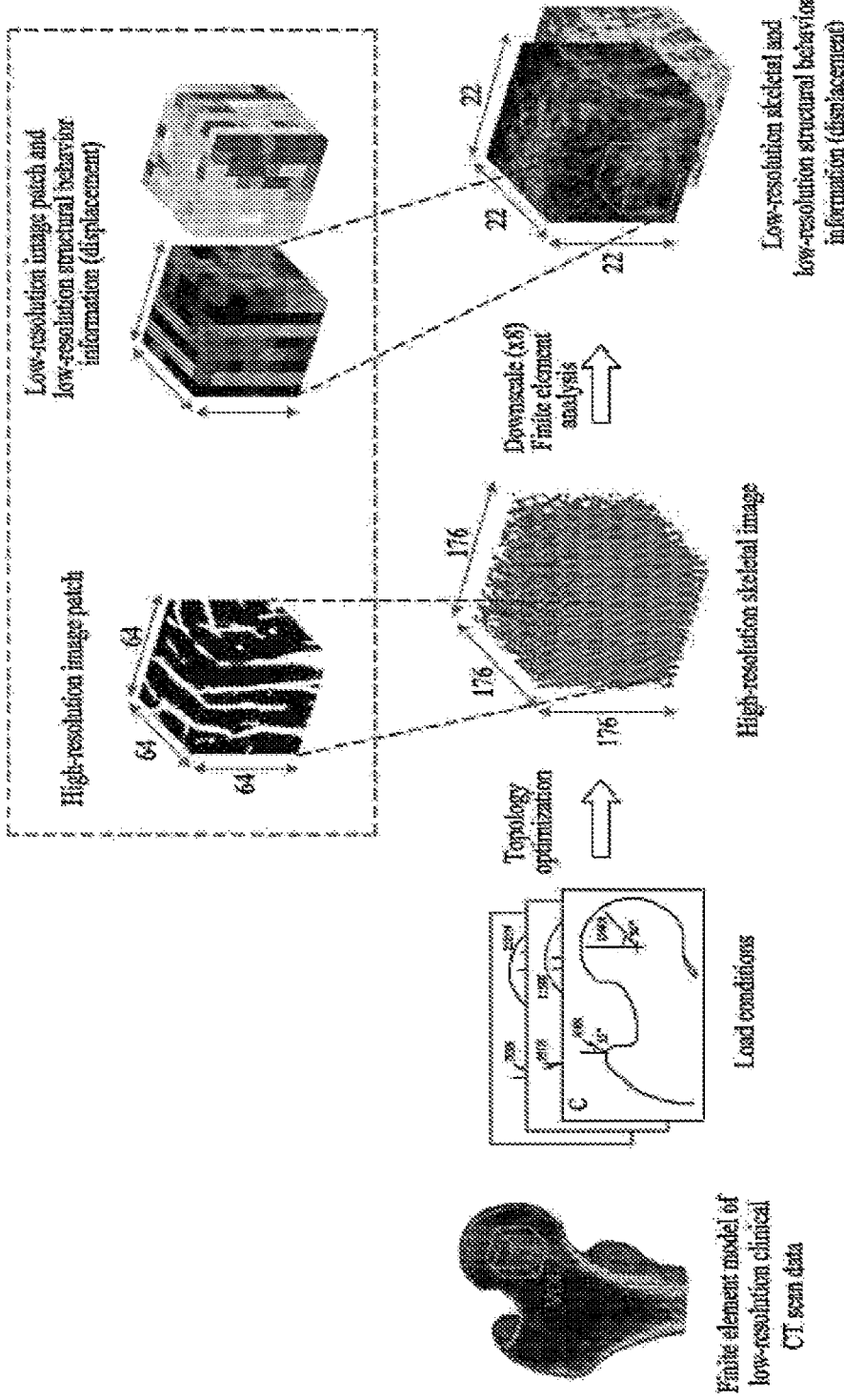
FIG. 4 illustrates an example of an operation of generating learning data of FIG. 3.
Figure 5:
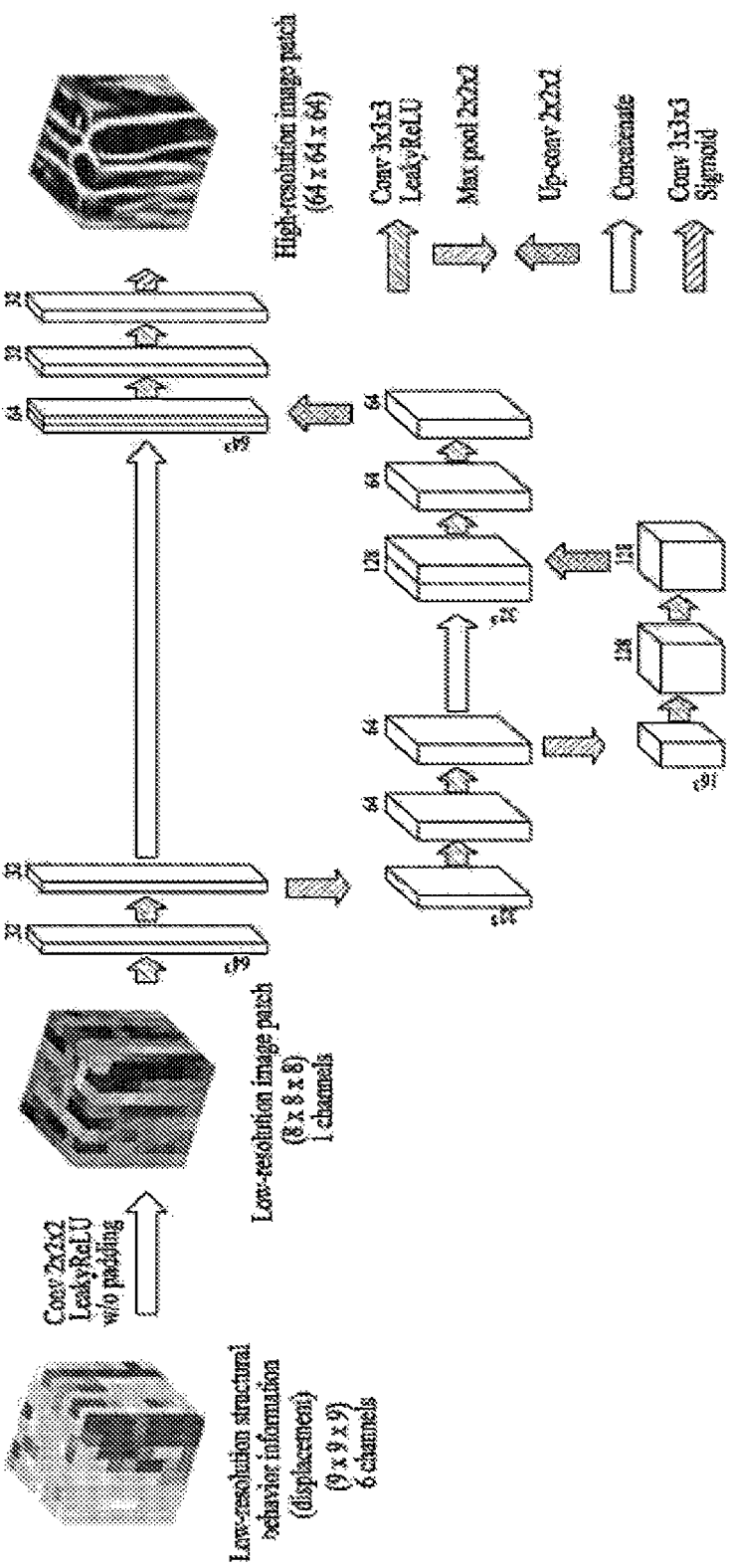
FIG. 5 illustrates an example of an operation of training the artificial neural network of FIG. 3.

FIG. 3 is a flowchart illustrating a method of training an artificial neural network of the computer device 100 according to various example embodiments. FIG. 4 illustrates an example of operation 310 of generating learning data of FIG. 3. FIG. 5 illustrates an example of operation 320 of training the artificial neural network of FIG. 3.

Referring to FIG. 3, in operation 310, the computer device 100 may generate a learning dataset. For learning of the artificial neural network, a high-resolution skeletal image capable of expressing a bone microstructure is required. Here, as described above, since the high-resolution skeletal image capable of expressing the bone microstructure is clinically uncapturable, it is not easy to secure a sufficiently large scale of learning datasets. In contrast, topology optimization may generate a learning dataset by enabling acquisition of various high-resolution skeletal images when applying different load conditions and BMD constraints to a low-resolution skeletal image. Topology optimization-based skeletal image reconstruction technology may perform reconstruction of a bone microstructure and accurate bone strength evaluation, however, has some limits in clinical application due to an excessive computation time. Therefore, it is expected that if it is possible to replace a topology optimization process with an artificial neural network, it is possible to reconstruct the bone microstructure with a level of precision and an amount of computation that are applicable to clinical application. Meanwhile, a skeletal system includes unit structures of a rod, a plate, and a junction, which represents that a structure of the skeletal system within an individual image is similar although a single image is divided into a plurality of partial images. When it is possible to train the artificial neural network with partial images, a large amount of learning data may be acquired from a small number of skeletal images. This represents that the artificial neural network may be trained to effectively learn the structure of the skeletal system.

Referring to FIG. 4, the processor 140 may perform topology optimization a total of N times, for example, ten times by applying different load conditions and BMD constraints to VOI in low-resolution clinical CT scan data and may acquire N bone microstructures, that is, high-resolution skeletal images for the VOL Here, the high-resolution skeletal images may be acquired in a predetermined size, for example, 176×176×176. Subsequently, the processor 140 may generate a learning dataset from the high-resolution skeletal images.

In detail, for example, referring to FIG. 4, the processor 140 may acquire low-resolution skeletal images at a clinical CT level for VOI by downscaling the high-resolution skeletal images by eight times. Here, the low-resolution skeletal images may be acquired in a predetermined size, for example, 22×22×22. Here, the processor 140 may acquire low-resolution structural behavior information (e.g., displacement) on the VOI by performing a finite element analysis on each of the low-resolution skeletal images. The processor 140 may segment each of the high-resolution skeletal images into a plurality of high-resolution image patches, may segment each of the low-resolution skeletal images into a plurality of low-resolution image patches, and may detect low-resolution structural behavior information on each of the low-resolution image patches. Here, the high-resolution image patches may be acquired in a predetermined size, for example, 64×64×64, and the low-resolution image patches may be acquired in a predetermined size, for example, 8×8×8. Through this, referring to FIG. 4, the processor 140 may generate a learning dataset having a plurality of data pairs, and each data pair may include a high-resolution image patch and a low-resolution image patch corresponding to each other, and low-resolution structural behavior information on the low-resolution image patch.

In some example embodiments, the processor 140 may increase the learning dataset by applying data augmentation through rotation of the high-resolution skeletal images. Through this, for example, the learning dataset having a total of 51,200 data pairs may be generated from a total of ten high-resolution skeletal images.

In operation 320, the computer device 100 may train the artificial neural network based on the learning dataset. In response to the low-resolution image patch and low-resolution structural behavior information on the low-resolution image patch being input to the artificial neural network, the processor 140 may train the artificial neural network such that the high-resolution image patch may be output from the artificial neural network. Here, the processor 140 may classify the learning dataset into a training dataset and a verification and test dataset. For example, the processor 140 may assign the learning dataset related to a portion of N high-resolution skeletal images, for example, six high-resolution skeletal images among a total of ten high-resolution skeletal images as the training dataset and may assign the learning dataset related to remaining high-resolution images as the verification and test dataset. The processor 140 may train the artificial neural network using the training dataset and then verify and test the trained artificial neural network using the verification and test dataset. As shown in FIG. 5, U-net showing high accuracy in a segmentation problem of a medical image may be used as the artificial neural network. Since skeletal image reconstruction may be viewed as a segmentation problem of an image that includes two phases, bone and marrow, the use of U-net may be appropriate. For example, learning may be performed with a mean square error (MSE) loss function, a batch size of 40, and a learning rate of 0.001.

Figure 6:
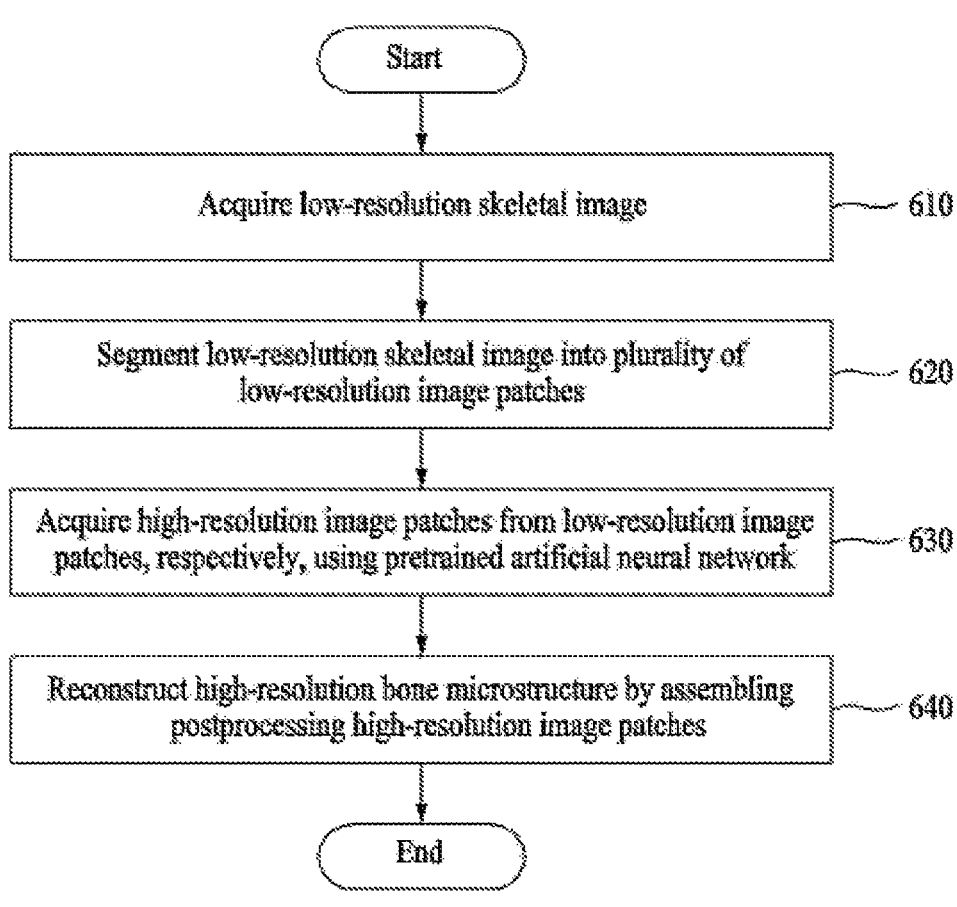
FIG. 6 is a flowchart illustrating a method for patch-wise 3D bone microstructure reconstruction of a computer device according to various example embodiments.
Figure 7:
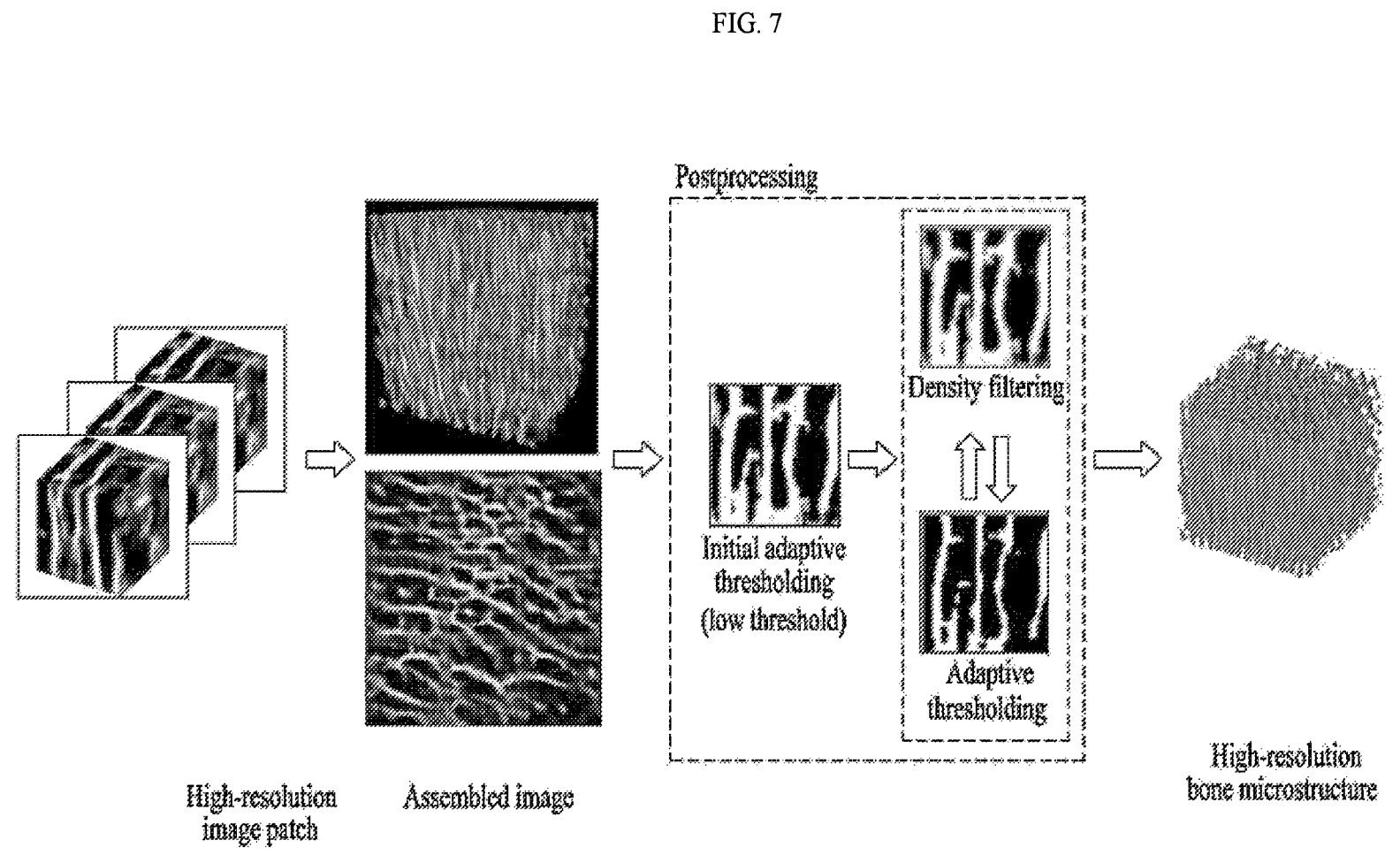
Figure 8:
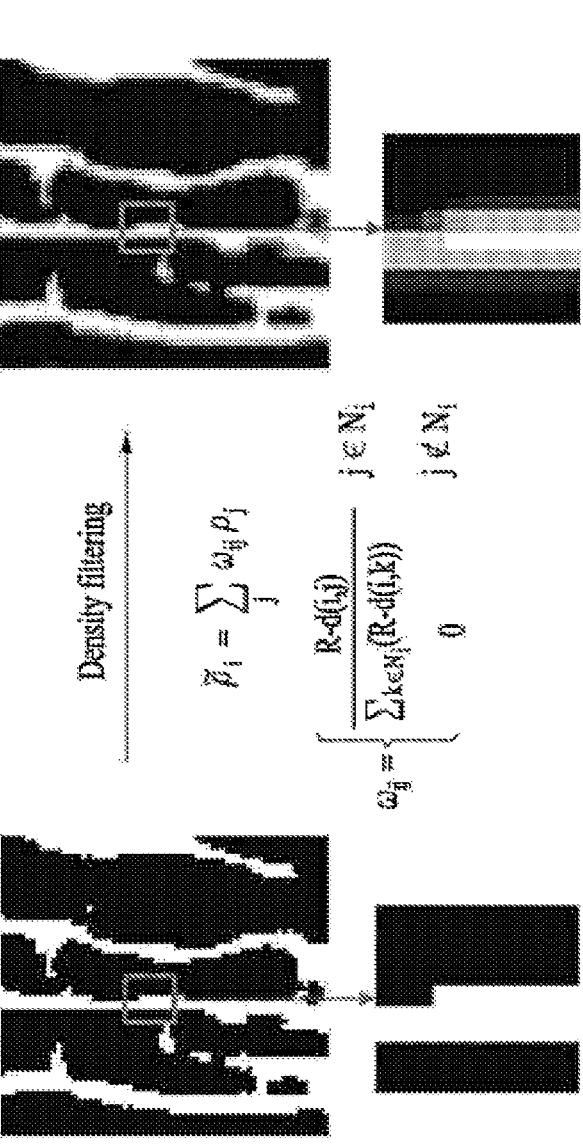
FIG. 8 illustrates an example of density filtering of FIG. 7.

FIG. 6 is a flowchart illustrating a method for patch-wise 3D bone microstructure reconstruction of the computer device 100 according to various example embodiments. FIG. 7 illustrates an example of an operation of reconstructing a 3D bone microstructure by assembling and postprocessing high-resolution image patches of FIG. 6. FIG. 8 illustrates an example of density filtering of FIG. 7, and FIG. 9 illustrates an example of adaptive thresholding of FIG. 7.

Referring to FIG. 6, in operation 610, the computer device 100 may acquire a low-resolution skeletal image to be reconstructed. The processor 140 may acquire a low-resolution skeletal image corresponding to VOI from low-resolution clinical CT scan data. Here, the low-resolution skeletal image may be acquired in a predetermined size, for example, 22×22×22 of FIG. 2. Here, the processor 140 may acquire low-resolution structural behavior information (e.g., displacement) on the VOI by performing a finite element analysis on the low-resolution skeletal image.

In operation 620, the computer device 100 may segment the low-resolution skeletal image into a plurality of low-resolution image patches. The processor 140 may acquire low-resolution image patches by sampling the low-resolution skeletal image. Here, the low-resolution image patches may be acquired in a predetermined size, for example, 8×8×8 of FIG. 2. Here, the processor 140 may acquire low-resolution structural behavior information on each of the low-resolution image patches.

In operation 630, the computer device 100 may acquire a plurality of high-resolution image patches from the low-resolution image patches, respectively, using a pretrained artificial neural network. As described above, the processor 140 may acquire the high-resolution image patches by training the low-resolution image patches using the trained artificial neural network, respectively. Here, the high-resolution image patches may be acquired in a predetermined size, for example, 64×64×64.

In operation 640, the computer device 100 may reconstruct a 3D high-resolution bone microstructure by assembling and postprocessing the high-resolution image patches. Referring to FIG. 7, the processor 140 may acquire an assembled image by assembling the high-resolution image patches. Here, an artificial discontinuity occurs in an overlapping area between the high-resolution image patches, which may hinder load propagation through a corresponding path and negatively affect accuracy of bone strength evaluation accordingly. Therefore, referring to FIG. 7, to clearly express a connectivity between high-resolution image patches and to remove a discontinuity between the high-resolution image patches, the processor 140 may perform postprocessing of repeatedly applying density filtering and adaptive thresholding on the assembled image. As a result, a more accurate high-resolution bone microstructure may be reconstructed from the assembled image, which may lead to improving the accuracy of the bone strength evaluation. Here, the high-resolution bone microstructure may be reconstructed in a predetermined size, for example, 176×176× 176.

In various example embodiments, referring to FIG. 8, the processor 140 may mitigate the artificial discontinuity by expressing BMD of a specific voxel as a weighted sum of neighboring BMD values through the density filtering. Meanwhile, the processor 140 may binarize an image through thresholding and convert BMD of the binarized image to have a distribution of [0, 1] such that thresholding may be applied again. Iterative density filtering and thresholding refers to a process of reconstructing an initial unclear BMD distribution into a clear bone microstructure.

Here, the processor 140 may binarize the image through adaptive thresholding. The adaptive thresholding may use a different "optimal" threshold value for each position of the image rather than a single "fixed" threshold value. Referring to FIG. 9, the processor 140 may compute a threshold value for each position using a BMD distribution of a low-resolution skeletal image such that a thresholding result of the image may have the same BMD distribution as that of the low-resolution skeletal image. Through this, patient-specific BMD distribution information on the low-resolution skeletal image may be used. The processor 140 may use a threshold value lower than a threshold value that is computed for initial one-time adaptive thresholding. Through this, the connectivity between the high-resolution image patches may be secured and accuracy of structural strength evaluation may be improved.

Various example embodiments of the present disclosure may quickly and accurately reconstruct a high-resolution bone microstructure from low-resolution clinical CT scan data using the artificial neural network. Here, since it is possible to minimize occurrence of a discontinuous structure by assembling and postprocessing high-resolution image patches acquired through the artificial neural network, and to apply an individual characteristic of a patient, patient-specific bone strength evaluation may be performed with higher accuracy than before. For verification of technology of the present disclosure, two volumes of interest (test datasets) not used for training of the artificial neural network were used. The high-resolution bone microstructure reconstructed from the low-resolution skeletal image through the present disclosure was compared with a result of topology optimization. For quantitative evaluation, four bone morphometric indices, that is, a total bone volume, a trabecular thickness (Tb.Th), a trabecular separation (Tb. Sp), and a degree of anisotropy, and a bone strength index, that is, an apparent stiffness, were used. As a result of comparing bone microstructures reconstructed with the technology of the present disclosure and the topology optimization, respectively, it was verified that the two structures are very similar. In detail, the bone morphometric indices and the bone strength index showed high accuracy and the technology of the present disclosure significantly reduced an amount of time used for reconstruction to around 99% compared to the existing topology optimization-based technology.

The technology of the present invention may be applied as follows. First, the technology of the present disclosure may improve diagnostic accuracy on skeletal diseases. A current BMD-based osteoporosis diagnosis method has some issues in that bone strength evaluation is inaccurate due to non-reflection of "bone quality" information and a diagnosis result is variable depending on a BMD reference group. A skeletal image reconstruction method currently being studied has limitations in terms of computation cost (topology optimization method) or high-resolution capability (artificial neural network method). For clinical application, it is necessary to develop novel technology capable of quickly providing a high-resolution magnification by overcoming the limitations. Here, the present disclosure may outperform an artificial structural discontinuity issue found in artificial neural network-based skeletal image high resolution technology and may provide accurate bone microstructure information required for diagnosis of osteoporosis. Second, the technology of the present disclosure may be applied to drug prescription for skeletal system-related diseases. Bisphosphonate, tibolone, denosumab, and the like, are currently used for treatment of osteoporosis and effectiveness of drugs are usually determined in terms of an increase or a decrease in bone mass. Here, the accurate effect of an individual drug on a bone microstructure is not specified and, to this end, in-vivo bone microstructure information needs to be acquired. When an accurate bone microstructure is expressed through the technology of the present invention, the effect of an individual drug on a bone microstructure may be more accurately determined. This represents that side effects of an individual patient may be minimized through patient-specific prescription.

Further, according to the present disclosure, the following effects may be predicted. In a technical aspect, physical limitations of a medical imaging device through image reconstruction may be overcome. Current medical imaging devices (e.g., CT, MRI, etc.) are limited to hundreds of $\mu m$ in terms of an acquirable in-vivo resolution due to limitations, such as an excessive radiation exposure and a long imaging time. The technology of the present disclosure may effectively express a bone microstructure through an image reconstruction method free from physical constraints and may provide bone microstructure-related information, such as accurate bone strength required in the clinical field of a skeletal system. The technology of the present disclosure relates to an image reconstruction method that is not restricted by a type of an imaging device and thus, may easily apply to constructed various medical imaging devices at relatively low cost. In addition, in a technical aspect, the reliability of early diagnosis of osteoporosis may be enhanced. Currently, osteoporosis is diagnosed with BMD-based relative evaluation. However, this method has a low diagnostic reliability since information on a bone microstructure is not reflected and it is impossible to accurately evaluate bone strength accordingly. The technology of the present disclosure enables an accurate bone strength evaluation by providing bone microstructure information through reconstruction of a medical image. Also, since low-dose and low-resolution medical images are used, long-term follow-up examinations may be performed, which may greatly contribute to enhancing the reliability of early diagnosis of osteoporosis.

In an economical/industrial aspect, medical cost related to osteoporosis may be reduced. Currently, the medical cost by an osteoporotic fracture in the United States reaches 18 billion dollars annually and the medical cost for osteoporosis treatment in Korea is also very high at 807.2 billion won.

Since the technology of the present disclosure may contribute the accurate diagnosis of osteoporosis, it is possible to preemptively and effectively respond to osteoporosis and osteoporotic fracture. If the reliable early diagnosis of osteoporosis is possible through the technology of the present disclosure, a reduction in the medical cost according to prevention of osteoporosis and a decrease in side effects according to overdiagnosis or misdiagnosis may be expected.

In a social aspect, the quality of life of people may be enhanced and national finances may be strengthened by improving the accuracy of diagnosis of osteoporosis. The osteoporotic fracture causes not only direct cost for treatment but also huge social cost, such as additional labor input for treatment of patients and loss of income due to early death of patients. As a result of research on data from the Korean Longitudinal Study of Aging (KLoSA), when a citizen aged 50 to 80 suffered from one case of osteoporotic fracture, an average of 70 million won in pension expenditure increased compared to a case without the fracture, while direct and indirect taxes decreased by an average of 53 million won. The technology of the present disclosure may contribute to a reliable early diagnosis and timely medical intervention related to osteoporosis and may prevent the occurrence of huge social cost by the osteoporotic fracture.

Various example embodiments provide a method and device for deep learning-based patch-wise 3D bone microstructure reconstruction from clinical CT scan data.

A method of the computer device 100 of various example embodiments may include segmenting a low-resolution skeletal image into a plurality of low-resolution image patches, acquiring a plurality of high-resolution image patches from the low-resolution image patches, respectively, using a pretrained artificial neural network, and reconstructing a high-resolution bone microstructure by assembling and postprocessing the high-resolution image patches.

According to various example embodiments, the low-resolution skeletal image may be acquired from a VOI in low-resolution clinical CT scan data.

According to various example embodiments, the method of the computer device 100 may further include training an artificial neural network.

According to various example embodiments, the training of the artificial neural network may include acquiring a plurality of high-resolution skeletal images by performing topology optimization by applying different load conditions and BMD constraints to a VOI in low-resolution clinical CT scan data, generating a learning dataset from the high-resolution skeletal images, and training the artificial neural network based on the learning dataset.

According to various example embodiments, the generating of the learning dataset may include acquiring a plurality of low-resolution skeletal images by downscaling the high-resolution skeletal images, respectively, acquiring low-resolution structural behavior information by performing a finite element analysis on each of the low-resolution skeletal images, and generating the learning dataset by segmenting each of the high-resolution skeletal images into a plurality of high-resolution image patches, by segmenting each of the low-resolution skeletal images into a plurality of low-resolution image patches, and by segmenting the low-resolution structural behavior information into a plurality of low-resolution image patches.

According to various example embodiments, the training of the artificial neural network may further include additionally acquiring at least one high-resolution skeletal image through rotation of at least one of the high-resolution skeletal images, thereby increasing the learning dataset.

According to various example embodiments, the method of the computer device 100 may further include acquiring low-resolution structural behavior information by performing a finite element analysis on the low-resolution skeletal image, and segmenting the low-resolution structural behavior information for each of the low-resolution image patches. The artificial neural network may be configured to output each of the high-resolution image patches in response to an input of each of the low-resolution image patches and the segmented low-resolution structural behavior information.

According to various example embodiments, the reconstructing of the high-resolution bone microstructure may include postprocessing an assembled image in which the high-resolution image patches are assembled to reconstruct the high-resolution bone microstructure.

According to various example embodiments, the postprocessing of the assembled image may include repeatedly applying density filtering that expresses BMD of a specific voxel as a weighted sum of BMD values of neighboring voxels and thresholding that binarizes an image.

According to various example embodiments, the thresholding may be adaptive thresholding that uses a different threshold value for each position of the image, and the threshold value may be computed such that a thresholding result for the image has the same BMD distribution as that of the low-resolution skeletal image.

The computer device 100 of various example embodiments may include the memory 130, and the processor 140 configured to connect to the memory 130 and to execute at least one instruction stored in the memory 130. The processor 140 may be configured to segment a low-resolution skeletal image into a plurality of low-resolution image patches, to acquire a plurality of high-resolution image patches from the low-resolution image patches, respectively, using a pretrained artificial neural network, and to reconstruct a high-resolution bone microstructure by assembling and postprocessing the high-resolution image patches.

According to various example embodiments, the low-resolution skeletal image may be acquired from a VOI in low-resolution clinical CT scan data.

According to various example embodiments, the processor 140 may be configured to acquire a plurality of high-resolution skeletal images by performing topology optimization by applying different load conditions and BMD constraints to a VOI in low-resolution clinical CT scan data, to generate a learning dataset from the high-resolution skeletal images, and to train an artificial neural network based on the learning dataset.

According to various example embodiments, the processor 140 may be configured to acquire a plurality of low-resolution skeletal images by downscaling the high-resolution skeletal images, respectively, to acquire low-resolution structural behavior information by performing a finite element analysis on each of the low-resolution skeletal images, and to generate the learning dataset by segmenting each of the high-resolution skeletal images into a plurality of high-resolution image patches, by segmenting each of the low-resolution skeletal images into a plurality of low-resolution image patches, and by segmenting the low-resolution structural behavior information into a plurality of low-resolution image patches.

According to various example embodiments, the processor 140 may be configured to additionally acquire at least one high-resolution skeletal image through rotation of at least one of the high-resolution skeletal images, thereby increasing the learning dataset.

According to various example embodiments, the processor 140 may be configured to acquire low-resolution structural behavior information by performing a finite element analysis on the low-resolution skeletal image, and to segment the low-resolution structural behavior information for each of the low-resolution image patches. The artificial neural network may be configured to output each of the high-resolution image patches in response to an input of each of the low-resolution image patches and the segmented low-resolution structural behavior information.

According to various example embodiments, the processor 140 may be configured to repeatedly apply density filtering that expresses BMD of a specific voxel as a weighted sum of BMD values of neighboring voxels and thresholding that binarizes an image, with respect to an assembled image in which the high-resolution image patches are assembled to reconstruct the high-resolution bone microstructure.

According to various example embodiments, the thresholding may be adaptive thresholding that uses a different threshold value for each position of the image, and the threshold value may be computed such that a thresholding result for the image has the same BMD distribution as that of the low-resolution skeletal image.

The methods according to the example embodiments may be provided as a computer program stored in non-transitory computer-readable recording media to implement various operations embodied by a computer. The media may continuously store a program executable by a computer or may temporarily store the same for execution or download. Also, the media may be various recording methods or storage methods in which single or a plurality of pieces of hardware are combined and may be distributed present over the network without being limited to media directly connected to a computer system. Examples of the media may include magnetic media such as hard disks, floppy disks, and magnetic tapes; optical media such as CD-ROM and DVDs: magneto-optical media such as floptical disks; and hardware devices that are specially designed to store program instructions, such as read-only memory (ROM), random access memory (RAM), and flash memory. Also, examples of other media may include an app store that distributes applications and recording media and storage media managed by a site, a server, and the like that supply and distribute various software.

The methods, operations, or techniques of the present disclosure may be implemented by various manners. For example, the techniques may be implemented by hardware, firmware, software, or combinations thereof. Those skilled in the art may understand that various logical blocks, modules, circuitries, and algorithm operations described in association with the disclosure herein may be implemented using electronic hardware, computer software, or combinations thereof. To clearly describe this interchange between hardware and software, various components, blocks, modules, circuitries, and operations are described above in terms of functions thereof. Whether such functions are implemented as hardware or implemented as software depends on design applications imposed to the overall system and a particular application. Those skilled in the art may implement the aforementioned functions in various manners for each specific application, but such implementations should not be interpreted as deviating from the scope of the present disclosure.

In hardware implementation, processing units used to perform the techniques may be implemented using one or more application-specific integrated circuits (ASIC)s, digital signal processors (DSP)s, digital signal processing devices (DSPDs), programmable logic devices (PLDs), field programmable gate arrays (FPGAs), processors, controllers, microcontrollers, microprocessors, electronic devices, other electronic units designed to perform the functions described herein, computer, or combinations thereof.

Therefore, various logic blocks, modules, and circuitries described in association with the present disclosure may be implemented or performed in any combination with a general-purpose processor, a DSP, an ASIC, an FPGA, or other programmable logic devices, a discrete gate or transistor logic, discrete hardware components, or devices designed to perform functions described herein. The general-purpose processor may be a microprocessor and, alternatively, the processor may be a conventional processor, a controller, a microcontroller, or a state machine. The processor may be implemented using a combination of computing devices, for example, a DSP and a microprocessor, a plurality of microprocessors, and one or more microprocessors associated with a DSP core, or a combination of other components.

In firmware and/or software implementation, the techniques may be implemented as instructions stored in non-transitory computer-readable recording media, such as random access memory (RAM), read-only memory (ROM), non-volatile random access memory (NVRAM), programmable read-only memory (PROM), erasable programmable read-only memory (EPROM), electrically erasable PROM (EEPROM), flash memory, compact disc (CD), and a magnetic or optical data storage device. The instructions may be executable by one or more processors and may cause the processor(s) to perform specific aspects of the functions described herein.

Although the example embodiments are described as using aspects of the currently disclosed subject matter in one or more stand-alone computer systems, the present disclosure is not limited thereto and may be implemented in conjunction with an arbitrary computing environment, such as network or distributed computing environment. Also, aspects of the subject matter in the present disclosure may be implemented in a plurality of processing chips or devices, and storage may be similarly affected across the plurality of devices. The devices may include PCs, network servers, and portable devices.

Although the present disclosure is described with respect to some example embodiments, various modifications and changes may be made without departing from the scope of the present disclosure that may understood by those skilled in the art. Also, such modifications and changes should be understood to fall within the scope of the claims.

What is claimed is:

1. A method of a computer device, the method comprising:

segmenting a low-resolution skeletal image into a plurality of low-resolution image patches;

acquiring a plurality of high-resolution image patches from the low-resolution image patches, respectively, using a pretrained artificial neural network; and reconstructing a high-resolution bone microstructure by assembling and postprocessing the high-resolution image patches, wherein the reconstructing comprises, postprocessing an assembled image in which the high-resolution image patches are assembled, to reconstruct the high-resolution bone microstructure,

wherein the postprocessing comprises, applying, on the assembled image, thresholding to binarize the assembled image; and applying, on the binarized assembled image, density filtering that expresses a bone mineral density (BMD) of a specific voxel as a weighted sum of BMD values of neighboring voxels, to generate a postprocessed assembled image having a BMD distribution of [0, 1] based on the binarized assembled image, wherein the applying of the thresholding and the applying of the density filtering on the postprocessed assembled image are repeatedly performed, wherein the applying of the thresholding comprises, binarizing the assembled image using threshold values each of which is computed for each position of the assembled image based on a BMD distribution of the low-resolution skeletal image, wherein a threshold value for said each position is computed as a smaller value as the applying of the thresholding is repeated.

2. The method of claim 1, wherein the low-resolution skeletal image is acquired from a volume of interest (VOI) in low-resolution clinical CT scan data.

3. The method of claim 1, further comprising:

training an artificial neural network, wherein the training of the artificial neural network comprises:

acquiring a plurality of high-resolution skeletal images by performing topology optimization by applying different load conditions and bone mineral density (BMD) constraints to a VOI in low-resolution clinical CT scan data;

generating a learning dataset from the high-resolution skeletal images; and training the artificial neural network based on the learning dataset.

4. The method of claim 3, wherein the generating of the learning dataset comprises:

acquiring a plurality of low-resolution skeletal images by downscaling the high-resolution skeletal images, respectively;

acquiring low-resolution structural behavior information by performing a finite element analysis on each of the low-resolution skeletal images; and generating the learning dataset by segmenting each of the high-resolution skeletal images into a plurality of high-resolution image patches, by segmenting each of the low-resolution skeletal images into a plurality of low-resolution image patches, and by segmenting the low-resolution structural behavior information into a plurality of low-resolution image patches.

5. The method of claim 3, wherein the training of the artificial neural network further comprises additionally acquiring at least one high-resolution skeletal image through rotation of at least one of the high-resolution skeletal images, thereby increasing the learning dataset.

6. The method of claim 1, further comprising:

acquiring low-resolution structural behavior information by performing a finite element analysis on the low-resolution skeletal image; and segmenting the low-resolution structural behavior information for each of the low-resolution image patches, wherein the artificial neural network is configured to output each of the high-resolution image patches in response to an input of each of the low-resolution image patches and the segmented low-resolution structural behavior information.

7. A computer device comprising:

a memory; and a processor configured to connect to the memory and to execute at least one instruction stored in the memory, wherein the processor is configured to, segment a low-resolution skeletal image into a plurality of low-resolution image patches, acquire a plurality of high-resolution image patches from the low-resolution image patches, respectively, using a pretrained artificial neural network, and reconstruct a high-resolution bone microstructure by assembling and postprocessing the high-resolution image patches, wherein the processor is configured to postprocess an assembled image in which the high-resolution image patches are assembled, to reconstruct the high-resolution bone microstructure, wherein the processor is configured to postprocess the assembled image by applying, on the assembled image, thresholding to binarize the assembled image; and applying, on the binarized assembled image, density filtering that expresses a bone mineral density (BMD) of a specific voxel as a weighted sum of BMD values of neighboring voxels, to generate a postprocessed assembled image having a BMD distribution of [0, 1] based on the binarized assembled image, wherein the applying of the thresholding and the applying of the density filtering on the postprocessed assembled image are repeatedly performed, wherein the applying of the thresholding comprises, binarizing the assembled image using threshold values each of which is computed for each position of the assembled image based on a BMD distribution of the low-resolution skeletal image, wherein a threshold value for said each position is computed as a smaller value as the applying of the thresholding is repeated.

8. The computer device of claim 7, wherein the low-resolution skeletal image is acquired from a volume of interest (VOI) in low-resolution clinical CT scan data.

9. The computer device of claim 7, wherein the processor is configured to, acquire a plurality of high-resolution skeletal images by performing topology optimization by applying different load conditions and bone mineral density (BMD) constraints to a VOI in low-resolution clinical CT scan data, generate a learning dataset from the high-resolution skeletal images, and train an artificial neural network based on the learning dataset.

10. The computer device of claim 9, wherein the processor is configured to, acquire a plurality of low-resolution skeletal images by downscaling the high-resolution skeletal images, respectively, acquire low-resolution structural behavior information by performing a finite element analysis on each of the low-resolution skeletal images, and generate the learning dataset by segmenting each of the high-resolution skeletal images into a plurality of high-resolution image patches, by segmenting each of the low-resolution skeletal images into a plurality of low-resolution image patches, and by segmenting the low-resolution structural behavior information into a plurality of low-resolution image patches.

11. The computer device of claim 9, wherein the processor is configured to additionally acquire at least one high-resolution skeletal image through rotation of at least one of the high-resolution skeletal images, thereby increasing the learning dataset.

12. The computer device of claim 7, wherein the processor is configured to, acquire low-resolution structural behavior information by performing a finite element analysis on the low-resolution skeletal image, and segment the low-resolution structural behavior information for each of the low-resolution image patches, and the artificial neural network is configured to output each of the high-resolution image patches in response to an input of each of the low-resolution image patches and the segmented low-resolution structural behavior information.

13. A non-transitory computer-readable recording medium storing instructions that, when executed by a processor, cause the processor to perform a method of acquiring a high-resolution bone microstructure, the method comprising:

segmenting a low-resolution skeletal image into a plurality of low-resolution image patches;

acquiring a plurality of high-resolution image patches from the low-resolution image patches, respectively, using a pretrained artificial neural network; and reconstructing a high-resolution bone microstructure by assembling and postprocessing the high-resolution image patches, wherein the reconstructing comprises, postprocessing an assembled image in which the high-resolution image patches are assembled, to reconstruct the high-resolution bone microstructure, wherein the postprocessing comprises, applying, on the assembled image, thresholding to binarize the assembled image; and applying, on the binarized assembled image, density filtering that expresses a bone mineral density (BMD) of a specific voxel as a weighted sum of BMD values of neighboring voxels, to generate a postprocessed assembled image having a BMD distribution of [0, 1] based on the binarized assembled image, wherein the applying of the thresholding and the applying of the density filtering on the postprocessed assembled image are repeatedly performed, wherein the applying of the thresholding comprises, binarizing the assembled image using threshold values each of which is computed for each position of the assembled image based on a BMD distribution of the low-resolution skeletal image, wherein a threshold value for said each position is computed as a smaller value as the applying of the thresholding is repeated.

14. The non-transitory computer-readable recording medium of claim 13, wherein the low-resolution skeletal image is acquired from a volume of interest (VOI) in low-resolution clinical CT scan data.

\* \* \* \* \*